(12) United States Patent
Duddu et al.

(10) Patent No.: US 8,133,993 B1
(45) Date of Patent: Mar. 13, 2012

(54) HYDROGENOLYTIC DENITRATION OF POLYNITRO COMPOUNDS: PENTANITROHEXAAZAISOWURTZITANE

(75) Inventors: Raja Duddu, Hackettstown, NJ (US); Paritosh Dave, Bridgewater, NJ (US); Reddy Damavarapu, Hackettstown, NJ (US); Rao Surapaneni, Long Valley, NJ (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 665 days.

(21) Appl. No.: 12/323,831

(22) Filed: Nov. 26, 2008

Related U.S. Application Data

(62) Division of application No. 11/162,737, filed on Sep. 21, 2005, now abandoned.

(51) Int. Cl.
*C07D 255/00* (2006.01)
*F42B 15/34* (2006.01)

(52) U.S. Cl. ..................................... 540/554

(58) Field of Classification Search .................... 540/554
See application file for complete search history.

(56) References Cited

OTHER PUBLICATIONS

Archibald et al., Synthesis of Polynitro-Cyclobutane Derivatives, J. Org. Chem., vol. 54, No. 12, pp. 2869-2873, 1989.*
Bull et al., Nitro-Steroids: Par-Il; A New Route to Nitro Steroids, J. Chem. Soc., pp. 2601-2614, 1965.*

* cited by examiner

*Primary Examiner* — Brenda Coleman
(74) *Attorney, Agent, or Firm* — Henry S. Goldfine

(57) ABSTRACT

A method for synthesizing pentanitrohexaazaisowurtzintane under neutral reaction conditions. Which synthesis involves treating a solution of hexanitrohexaazaisowurtzitane in ethyl acetate in the presence of a catalytic quantity of palladium on a carbon substrate, until a heterogeneous mixture is formed. This heterogeneous mixture is hydrogenated under a balloon atmosphere until the starting hexanitrohexaazaisowurtzitane is substantially reacted. The resulting pentanitrohexaazaisowurzitane mixture is filtered, dried and recovered from the dried residue through a Si-gel column.

1 Claim, No Drawings

HYDROGENOLYTIC DENITRATION OF POLYNITRO COMPOUNDS: PENTANITROHEXAAZAISOWURTZITANE

CROSS-REFERENCE TO RELATED APPLICATIONS

This application is a divisional of and claims priority from a copending prior U.S. patent application Ser. No. 11/162,737, filed Sep. 21, 2005, which copending prior application is hereby incorporated by reference, and which copending prior application claims priority to a previously filed, U.S. Provisional application, Ser. No. 60/522,369, filed Sep. 21, 2004, which provisional application is also incorporated herein by reference.

FEDERAL RESEARCH STATEMENT

The invention described herein may be made, used, or licensed by or for the United States Government for Government purposes without the payment of any royalties thereon or therefore.

BACKGROUND OF THE INVENTION

1. Field of the Invention

The present invention relates to hydrogenolytic denitration of polynitro compounds. In particular, the present invention relates to pentanitrohexaazaisowurtzitane.

2. Description of Related Art

Polynitro carbocycles and nitrogen containing heterocycles, due to their utility as energetic ingredients, are of intense current interest to defense agencies world wide. It is in this context that synthesis and development of new materials such as 1,1,3,3-tetranitrocyclobutane, 1,1,3-trinitroazetidine and hexaazaisowurtzitane has attracted the attention of synthetic organic chemists. In continuation of this work aimed at synthesis and development of new energetic ingredients, we attempted to synthesize pentanitrohexaazaisowurtzitane. It was in this connection that we studied the hydrogenation of 1,1,3,3-tetranitrocyclobutane and we further extended our hydrogenation experiments to hexanitrohezaazaisowurtzitane. The details of our hydrogenation experiments which resulted in the formation of 1,1,3-trinitrocyclobutane and pentanitrohexaazaisowurtzitane are described herein.

BRIEF SUMMARY OF THE INVENTION

Objects of the Invention

It is an object of the present invention to provide novel polynitro compounds with possible application as high explosives.

The other objects, features and advantages of the present invention will become more apparent in light of the following detailed description of the preferred embodiment thereof.

SUMMARY OF THE INVENTION

According to the present invention, there is provided pentanitrohexaazaisowurtzitane.

DETAILED DESCRIPTION OF THE INVENTION

According to the present Invention, there is provided pentanitrohexaazaisowurtzitane.

CL-20, a well-known polynitro polyaza polycyclic compound, has been in existence for the past two decades. Applications of this compound in munitions systems are aggressively being explored. One of the factors limiting its applications in munitions systems is its sensitivity. The sensitivity of CL-20 is unpredictable. In spite of serious efforts to solve the sensitivity issue, the problem still persists. In an effort to obtain a reduced sensitivity material while keeping the CL-20 core structure and much of the power, a new compound, pentanitrohexaazaisowurtzitane, was prepared. The aminoproton would be capable of forming hydrogen bonds with nitro groups (intra or inter molecularly). Such hydrogen bonding is known to reduce sensitivity of energetic materials such as TATB. CL-20 has been used as the starting substrate. In the reaction process, a nitro group was removed from the molecule thereby generating a new energetic material. The structure of the new compound has been established unambiguously via x-ray crystallography. The density of the material was found to be 1.907 gm/cc. This figure is much higher than HMX, but similar to one of the polymorphs of CL-20. Due to its inherent energetic nature, with high density, pentanitrohexaazaisowurtzitane could become an additive or replacement in several energetic formulations that use HMX or CL-20.

Polynitro carbocycles, such as, for example, octanitrocubane, are well known for their explosive properties. Although trinitrocyclobutane has been mentioned in the literature, due to the difficulty in its isolation, it has never been isolated or characterized to establish its physical, chemical and explosive properties. Trinitrocyclobutane has now been successfully prepared under neutral reaction conditions, isolated and characterized. An x-ray crystallographic study has been carried out to determine its density and other unit cell properties. This compound has a melting point of 99-100 degrees centigrade. Due to its low melting nature and the intense current interest in development of new melt cast explosives, trinitrocyclobutane would be a potential candidate compound for future melt cast applications.

A literature search to prepare the desired trinitrocyclobutane led to the report by Archibald and co-workers (Archibald, T. G.; Graver, L. C.; Baum, K.; Cohen, M. C.; Synthesis of polynitro-cyclobutane derivatives. J. Org. Chem., 1989, 54(12), 2869-2873.). Their report included preparation of several polynitrocyclobutane derivatives. However, trinitrocyclobutane was not isolated and characterized due to its reported instability. Hence, no data was provided for trinitrocyclobutane. Their attempts to prepare trinitrocyclobutane involved isolation of trinitrocyclobutane from either a reaction mixture of tetranitro and trinitro cyclobutanes or a direct oxidation of 3,3-dinitrociclobutylammonium chloride. There were no other reports available in the literature for the preparation of trinitrocyclobutane.

These literature findings prompted a search to find ways to prepare, isolate and characterize trinitrocyclobutane under neutral reaction conditions. Reduction methods are commonly employed for conversion of nitramino groups (N—$NO_2$) into their corresponding amines (N—H). Application of these reductive methods often tends to give the corresponding C—$NH_2$ groups when employed in the case of C—$NO_2$ compounds. However, Bull, et al., (Bull, J. R.; Jones, E. R.; Meakins, G. D.; Nitro-steroids: Par-II; A new route to nitro-steroids. J. Chem. Soc., 1965, 2601-2614.) reported the synthesis of nitro steroids via controlled hydrogenation of steroids containing gem-dinitro groups, the synthesis of by employing the method reported by Bull, et al. Hydrogenation of 1,1,3,3-tetranitrocyclobutane with a 10% pd-C at room temperature under atmospheric pressure resulted in the formation of the desired 1,1,3-trinitrocyclobutane. The pure product was isolated using standard purification techniques as a colorless solid. Interestingly, 1,1,3-trinitrocyclobutane was found to be stable and the structure of the product as 1,1,3-trinitrocyclobutane was established unambiguously via single crystal x-ray crystallography.

Application of the identical set of hydrogenation reaction conditions for hexanitrohexaazaisowurtzitane afforded pentanitrohexaazaisowurtzitane. The structure of this product was established unambiguously via single crystal x-ray crystallography. It is interesting to note that during the hydrogenation, the nitro group attached to the nitrogen in the five membered ring was replaced by hydrogen, leaving the nitro group in the boat-like six membered ring at the bottom untouched.

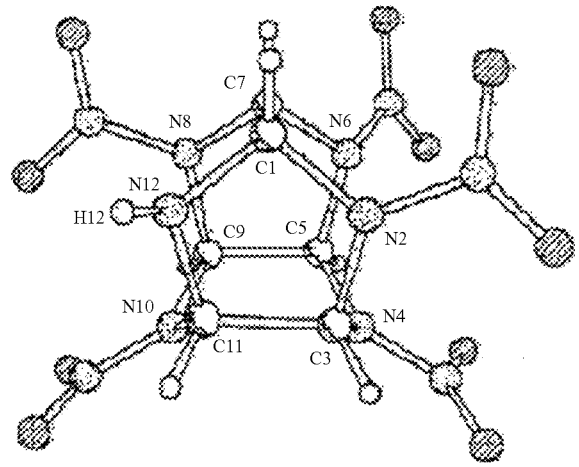

In summary, successful preparation and isolation of pentanitrohexaazaisowurtzitane under neutral reaction conditions, along with x-ray structural data are reported.

| X-ray Structure Data For: | Pentanitrohexaazaisowurtzitane |
| --- | --- |
| Empirical Formula | C6 H7 N11 O10 |
| Formula Weight | 393.23 |
| Space Group | P2(1)2(1)2(1) |
| Unit Cell Dimensions | A = 8.577(2) Å; $\square$ = 90° |
| | B = 12.075(3) Å; $\square$ = 90° |
| | C = 13.223(4) Å; $\square$ = 90° |
| Volume | 1369.5(6) Å$^3$ |
| Z | 4 |
| Density (Calculated) | 1.907 Mg/m$^3$ |
| Temperature | 293(2)K |
| Wavelength | 1.54178 Å |
| Crystal System | Orthorhombic |
| Absorption Coefficient | 1.603 mm$^{-1}$ |
| F(000) | 800 |
| Theta Range for Data Collection | 4.96 to 55.57° |
| Index Ranges | −8 <= h <= 9, −12, = k <= 10, −9 <= l <= 12 |

-continued

| X-ray Structure Data For: | Pentanitrohexaazaisowurtzitane |
| --- | --- |
| Reflections Collected | 4308 |
| Reflections "Observed" | 1177 [I > 2 sigma(I)] |
| Independent Reflections | 1506 [R(int) = 0.0653] |
| Completeness to theta = 28.94° | 92.5% |
| Absorption Correction | None |
| Refinement Method | Full-matrix least-squares on F$^2$ |
| Data/Restraints/Parameters | 1506/0/248 |
| Goodness-of-Fit of F$^2$ | 1.118 |
| Final R indices [I > 2 sigma(I)] | R1 = 0.0689, wR2 = 0.1649 |
| R indices (all data) | R1 − 0.0930, wR2 = 0.1855 |
| Largest cliff peak and hole | 0.353 and −0.275e. Å$^{-3}$ |

Example

A solution of hexanitrohexaazaisowurtzitane (2.11 mmol) in ethyl acetate was treated with 10% Pd—C (100 mg) and the resulting heterogeneous mixture was subjected to hydrogenation under balloon atmosphere. The progress of the reaction was monitored by thin layer chromatography. After the complete disappearance of the starting material (40% Ethyl acetate-hexanes), the reaction mixture was filtered and evaporated to dryness. The residue was passed through a Si-gel column (10% Ethyl acetate-hexanes) to obtain the pure product. A white solid (Yield: 52%) was obtained. $^1$H NMR (Acetone-d$_6$): 5.38 (t, J=6.82 Hz, 1H), 6.81 (t, J=6.19 Hz, 1H), 7.21 (dt, J=8.06, 2.91 Hz, 1H), 7.56 (dd, J=6.24, 1.14 Hz, 1H), 7.85 (dd, J=8.08, 2.65 Hz, 1H), 7.96 (dd, J=8.22, 2.94 Hz, 1H), 8.33 (ddd, J=8.22, 2.62, 1.37 Hz, 1H); $^{13}$C NMR (Acetone-d$_6$): 70.13, 70.85, 71.68, 72.81, 76.11, 76.56.

Other features, advantages, and specific embodiments of this invention will become readily apparent to those exercising ordinary skill in the art after reading the foregoing disclosures. These specific embodiments are within the scope of the claimed subject matter unless otherwise expressly indicated to the contrary. Moreover, while specific embodiments of this invention have been described in considerable detail, variations and modifications of these embodiments can be effected without departing from the spirit and scope of this invention as disclosed and claimed.

What is claimed is:

1. A method for preparing pentanitrohexaazaisowurzitane under neutral reaction conditions, said method comprising the steps of:
   a) treating a solution of hexanitrohexaazaisowurtzitane (2.11 mmol) in ethyl acetate with 10% Pd—C (100 mg) resulting in a heterogeneous mixture;
   b) subjecting the heterogeneous mixture to hydrogenation under balloon atmosphere while monitoring the progress of the reaction by thin layer chromatography;
   c) filtering the resulting reaction mixture and evaporating it to dryness; and
   d) recovering the pentanitrohexaazaisowurzitane from the dry residue by passing the residue through a Si-gel column.

* * * * *